United States Patent
Wilger et al.

(10) Patent No.: US 11,484,423 B2
(45) Date of Patent: Nov. 1, 2022

(54) APPARATUSES TO FACILITATE PROSTHESIS PLACEMENT

(71) Applicant: COOK MEDICAL TECHNOLOGIES LLC, Bloomington, IN (US)

(72) Inventors: Kevin Wilger, Lafayette, IN (US); Stephan Haulon, Paris (FR); Jarin Andrew Kratzberg, West Lafayette, IN (US); Blayne A. Roeder, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 342 days.

(21) Appl. No.: 16/107,082

(22) Filed: Aug. 21, 2018

(65) Prior Publication Data

US 2020/0060855 A1 Feb. 27, 2020

(51) Int. Cl.
| | |
|---|---|
| *A61F 2/954* | (2013.01) |
| *A61F 2/06* | (2013.01) |
| *A61F 2/856* | (2013.01) |
| *A61F 2/07* | (2013.01) |
| *A61F 2/89* | (2013.01) |

(Continued)

(52) U.S. Cl.
CPC .............. *A61F 2/954* (2013.01); *A61F 2/07* (2013.01); *A61F 2/89* (2013.01); *A61F 2/856* (2013.01); *A61F 2/962* (2013.01); *A61F 2/966* (2013.01); *A61F 2002/061* (2013.01); *A61F 2002/065* (2013.01)

(58) Field of Classification Search
CPC .... A61F 2/954; A61F 2/07; A61F 2/89; A61F 2/856; A61F 2002/061; A61F 2002/065; A61F 2/95; A61F 2/962; A61F 2/966
See application file for complete search history.

(56) References Cited

U.S. PATENT DOCUMENTS

| | | | |
|---|---|---|---|
| 6,854,467 | B2 | 2/2005 | Boekstegers |
| 7,575,590 | B2 | 8/2009 | Watson |
| 8,002,815 | B2 | 8/2011 | Laroya et al. |

(Continued)

FOREIGN PATENT DOCUMENTS

WO WO2009/149927 12/2009

*Primary Examiner* — Jing Rui Ou
(74) *Attorney, Agent, or Firm* — Crowell & Moring LLP

(57) ABSTRACT

Methods and apparatuses to place a prosthesis within a receiving structure are provided. A delivery apparatus includes an elongated support member including a support member distal end. A stop cap is disposed at the support member distal end and includes a stop cap transverse dimension larger than an inner diameter of a receiving lumen of the receiving structure. An elongated prosthesis-positioning member extends along the support member and stop cap so a distal surface of the prosthesis-positioning member is disposed at a position longitudinally coincident with a portion of the stop cap. A sheath comprises a sheath lumen receiving the prosthesis-positioning member so the sheath translates longitudinally relative to the prosthesis-positioning member. The delivery apparatus has a loaded configuration in which the prosthesis is received in the sheath lumen with a proximal end of the prosthesis abutting the prosthesis-positioning member distal surface.

10 Claims, 16 Drawing Sheets

(51) Int. Cl.
*A61F 2/966* (2013.01)
*A61F 2/962* (2013.01)

(56) References Cited

U.S. PATENT DOCUMENTS

| | | |
|---|---|---|
| 8,298,277 B2 | 10/2012 | Mangiardi et al. |
| 8,353,946 B2 | 1/2013 | Mangiardi et al. |
| 8,876,854 B2 | 11/2014 | Christiansen |
| 8,945,202 B2 | 2/2015 | Mayberry et al. |
| 9,050,437 B2* | 6/2015 | Shaked .................... A61F 2/954 |
| 9,101,456 B2 | 8/2015 | Hartley et al. |
| 9,572,696 B2 | 2/2017 | Schneider et al. |
| 2002/0091434 A1* | 7/2002 | Chambers ............... A61F 2/958 |
| | | 623/1.11 |
| 2003/0093145 A1* | 5/2003 | Lawrence-Brown ... A61F 2/954 |
| | | 623/1.21 |
| 2003/0199967 A1* | 10/2003 | Hartley .................... A61F 2/07 |
| | | 623/1.13 |
| 2004/0111143 A1* | 6/2004 | Fischell .................... A61F 2/95 |
| | | 623/1.11 |
| 2005/0010277 A1* | 1/2005 | Chuter ..................... A61F 2/07 |
| | | 623/1.13 |
| 2005/0101968 A1* | 5/2005 | Dadourian ................ A61F 2/95 |
| | | 606/108 |
| 2006/0184224 A1 | 8/2006 | Angel |
| 2006/0229697 A1* | 10/2006 | Gerdts ..................... A61F 2/95 |
| | | 623/1.11 |
| 2007/0173918 A1* | 7/2007 | Dreher .................... A61F 2/958 |
| | | 623/1.11 |
| 2008/0109056 A1* | 5/2008 | Chalekian ............... A61F 2/954 |
| | | 623/1.11 |
| 2008/0109058 A1 | 5/2008 | Greenberg et al. |
| 2012/0109279 A1* | 5/2012 | Mayberry ............... A61F 2/954 |
| | | 623/1.11 |
| 2012/0226341 A1* | 9/2012 | Schreck ................... A61F 2/07 |
| | | 623/1.12 |
| 2013/0204344 A1 | 8/2013 | Tatalovich et al. |
| 2015/0202068 A1 | 7/2015 | Arbefeuille et al. |
| 2017/0319365 A1* | 11/2017 | Dakak .................... A61F 2/954 |

* cited by examiner

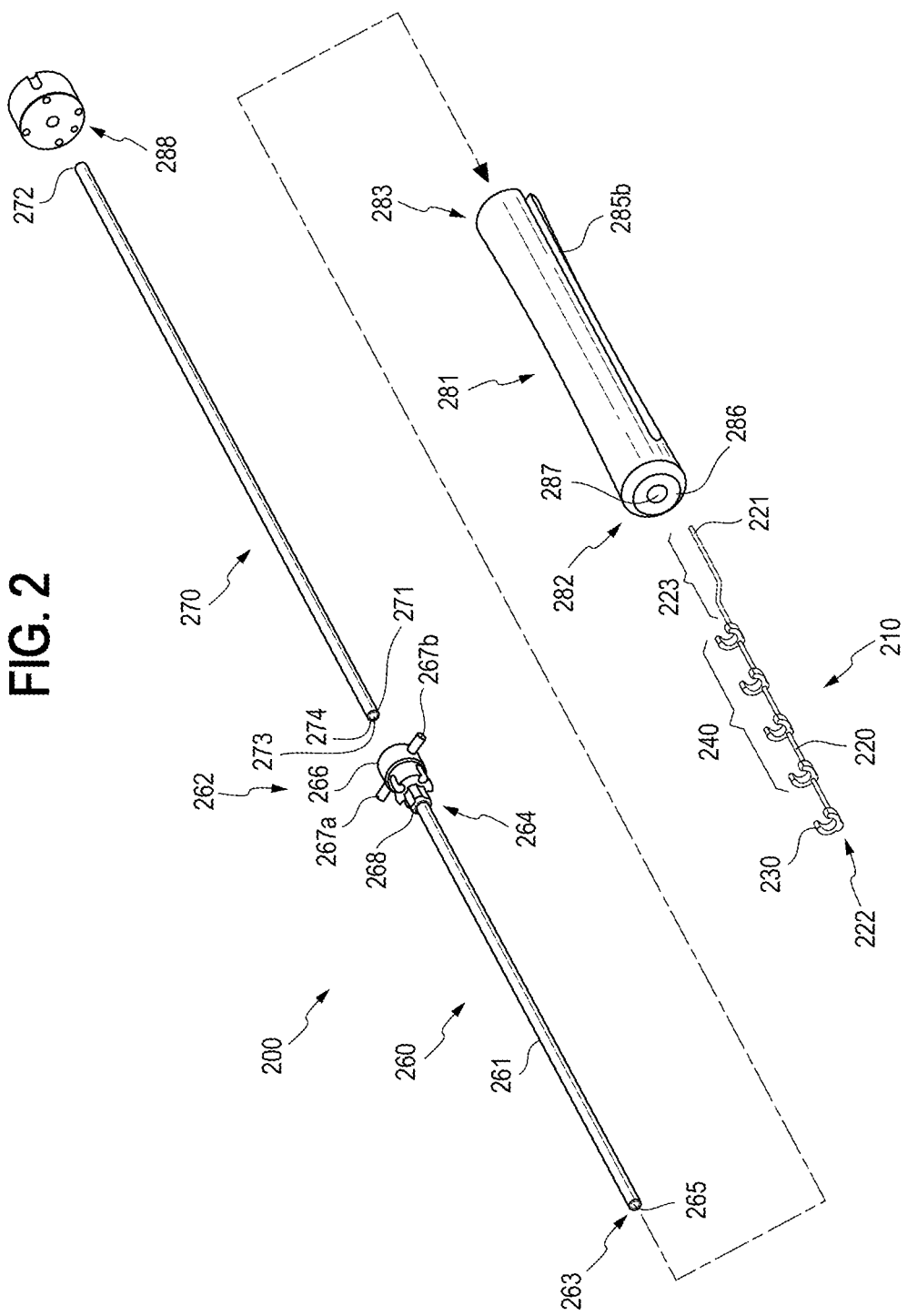

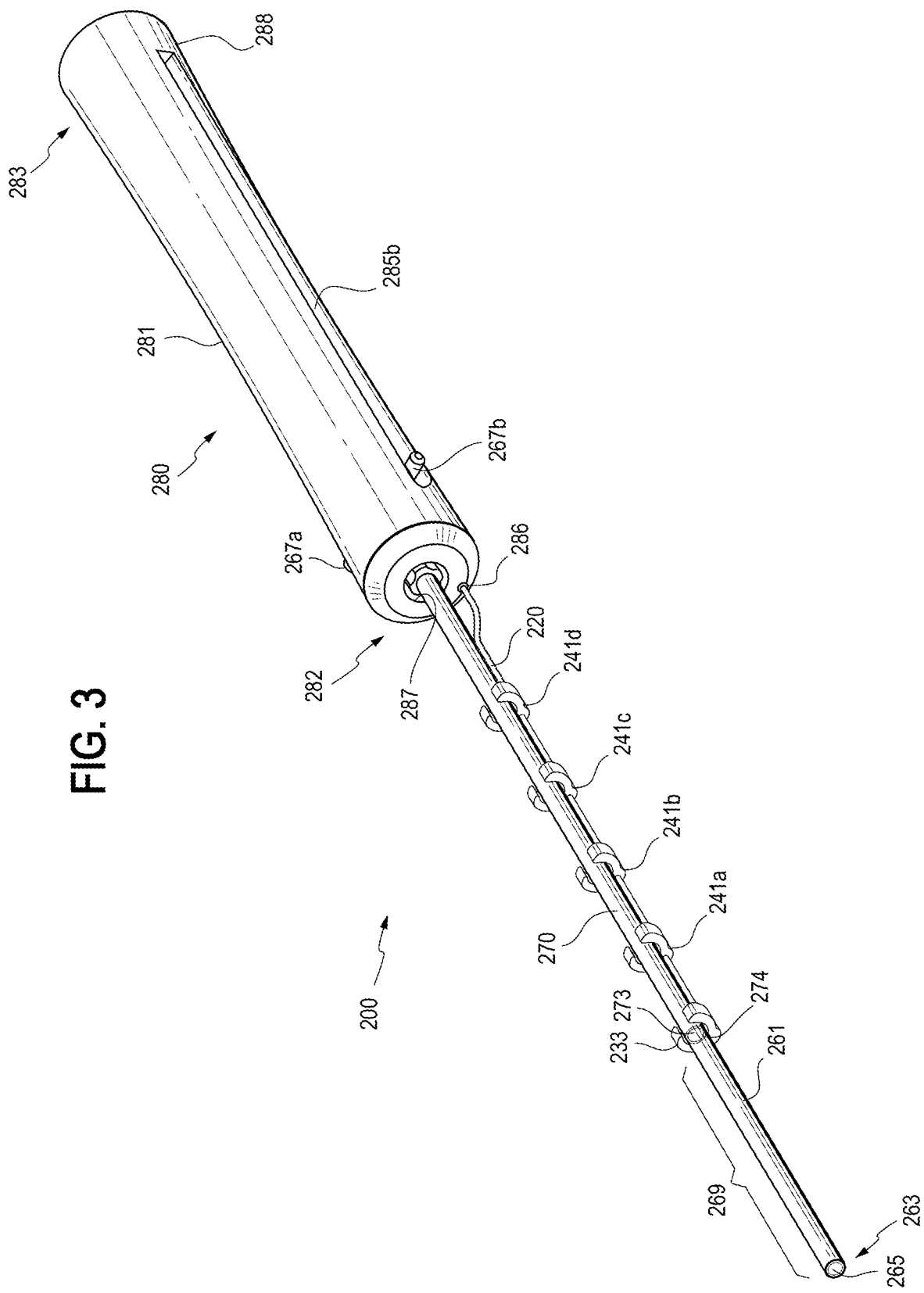

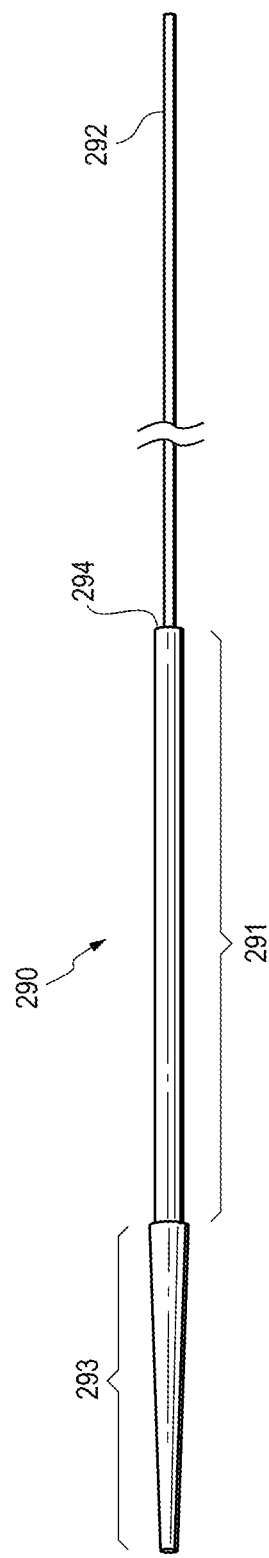

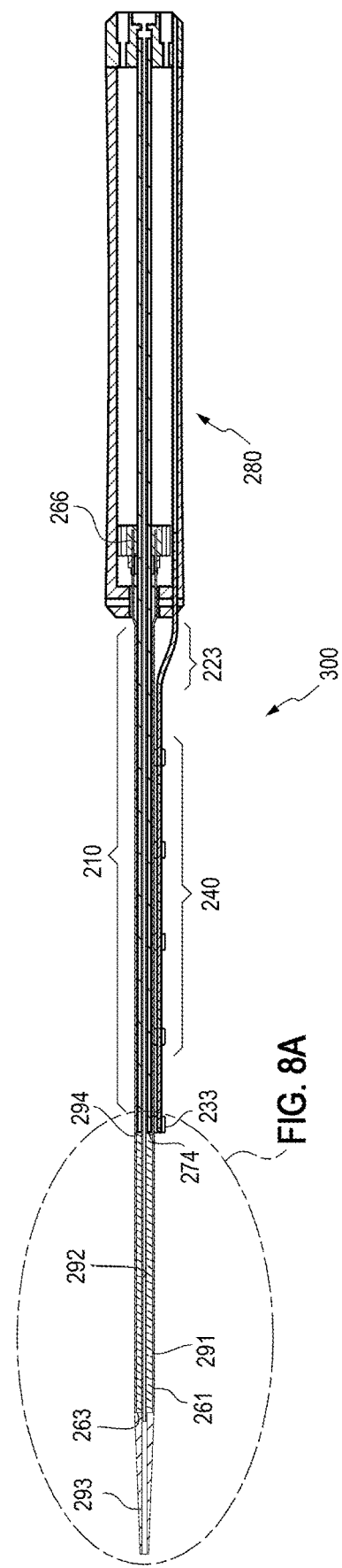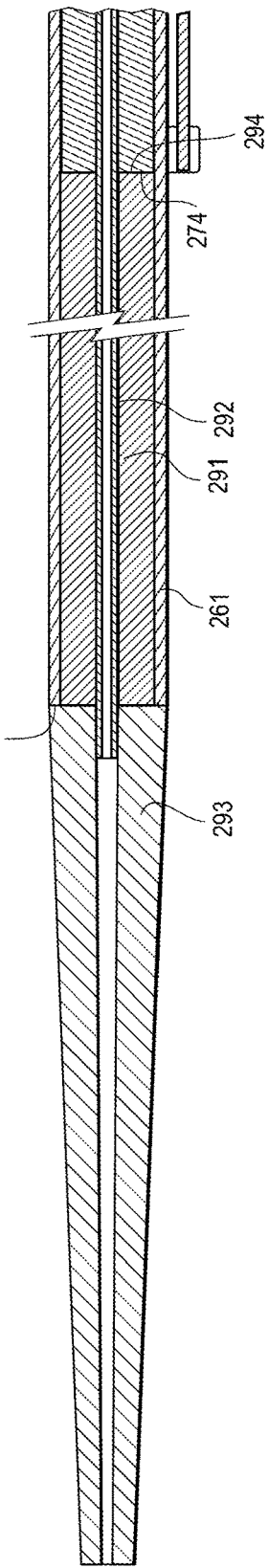

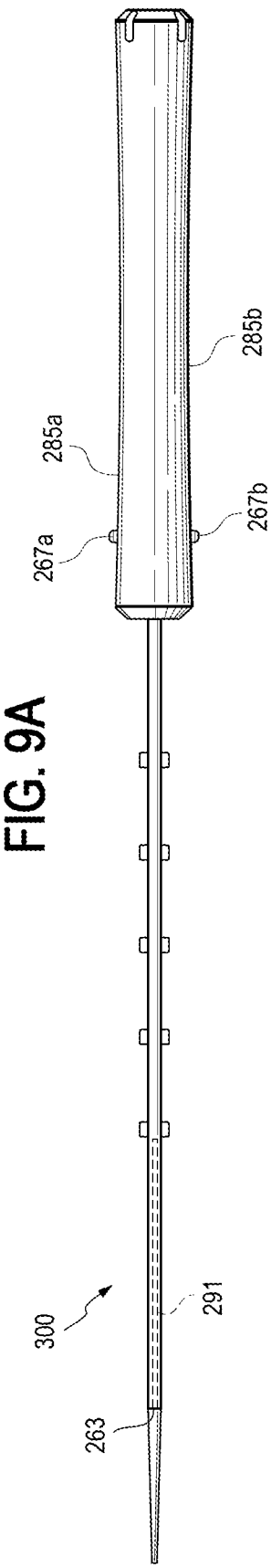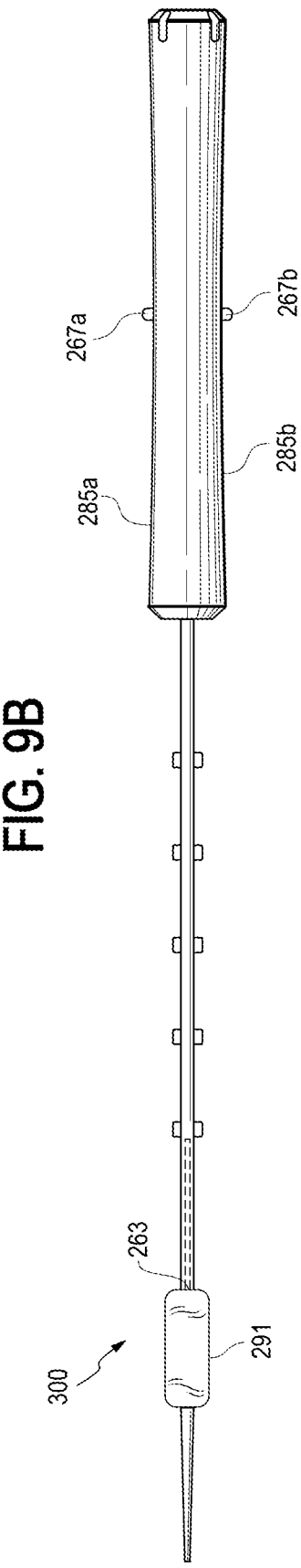

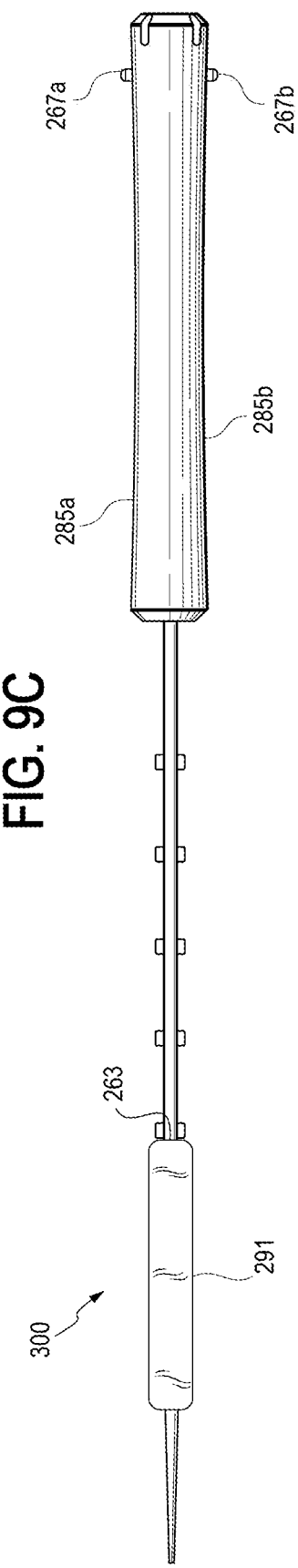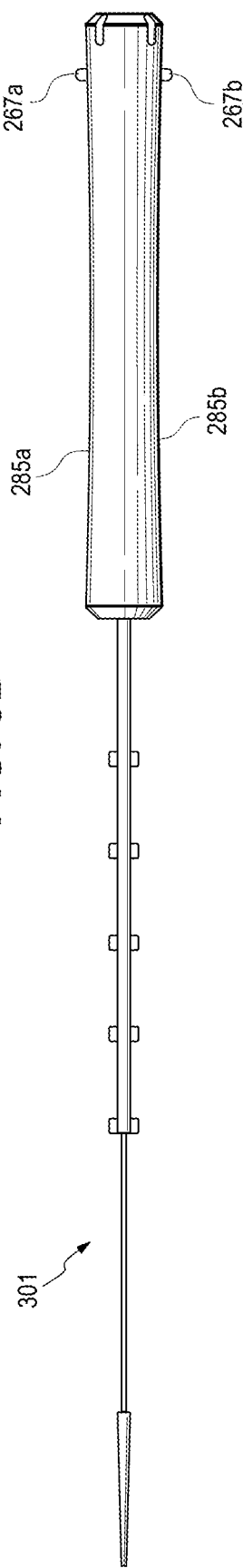

APPARATUSES TO FACILITATE PROSTHESIS PLACEMENT

BACKGROUND

Embodiments disclosed herein generally relate to medical devices. More particularly, embodiments disclosed herein relate to medical implant delivery apparatuses and methods, for example, apparatuses and methods to facilitate placement of prostheses within branch vessels.

Accurate and precise placement of a medical implant relative to one or more anatomical structures or other medical implants may improve the clinical results of a medical procedure. For example, a clinician may address a defect in a vessel by placing one or more prostheses (e.g., stents, stent-grafts, or grafts) within the vessel, e.g., to reinforce the vessel, keep the vessel open to fluid flow, connect the vessel to another prosthesis, etc. Accurate and precise placement of the prosthesis may ensure that fluid can flow in the desired manner or that the prosthesis is securely connected with the vessel or with another prosthesis. Certain characteristics of surgical procedures may however make it difficult for the clinician to accurately and precisely place a medical implant. For example, although in some surgical procedures fluoroscopy may allow the clinician to visualize the location of a medical device relative to the structure into which it is being placed, in other surgical procedures, e.g., cardiothoracic surgery, fluoroscopy may not be available to provide such guidance.

A frozen elephant trunk technique is an exemplary cardiothoracic surgery procedure in which the unavailability of fluoroscopy may make it difficult for the clinician to properly place a medical implant. A frozen elephant trunk technique may be used to treat a patient with an extensive aneurysm or dissection of the ascending aorta and descending aorta. Other surgical procedures may present similar or different characteristics that make it difficult for a clinician to accurately and precisely place medical implants in a desired manner.

Although many different variations of medical implant placement components and procedural steps have been introduced into the art, there exists a need for designs that allow clinicians to place medical implants in an improved manner.

SUMMARY

In one aspect of the present disclosure, a delivery apparatus to place a prosthesis within a receiving structure may be provided. The delivery apparatus includes an elongated support member including a support member distal end. The delivery apparatus further includes a stop cap disposed at the support member distal end, the stop cap including a stop cap transverse dimension that is larger than an inner diameter of a receiving lumen defined by the receiving structure. The delivery apparatus further includes an elongated prosthesis-positioning member including a prosthesis-positioning member distal surface and extending along the support member and the stop cap so that a distal surface of the prosthesis-positioning member is disposed at a position longitudinally coincident with a portion of the stop cap. The delivery apparatus further includes a sheath comprising a sheath lumen, the sheath lumen receiving the prosthesis-positioning member so that the sheath translates longitudinally relative to the prosthesis-positioning member. The delivery apparatus has a loaded configuration in which the prosthesis is received in the sheath lumen with a proximal end of the prosthesis abutting the prosthesis-positioning member distal surface.

In a second aspect of the present disclosure, a delivery apparatus to place a prosthesis within a receiving structure may be provided. The delivery apparatus includes an elongated support member comprising a support member distal end. The delivery apparatus further includes a stop cap coupled to the support member distal end, the stop cap including a stop cap transverse dimension that is larger than an inner diameter of a receiving lumen defined by the receiving structure. The delivery apparatus further includes a spine portion including at least one spine member coupled to the support member, the at least one spine member located between the stop cap and the handle. The delivery apparatus further includes an elongated prosthesis-positioning member including a prosthesis-positioning member distal surface. The delivery apparatus further includes a sheath comprising a sheath lumen, the sheath lumen receiving the prosthesis-positioning member so that the sheath translates longitudinally relative to the prosthesis-positioning member. The delivery apparatus has a loaded configuration in which the prosthesis is received in the sheath lumen with a proximal end of the prosthesis abutting the prosthesis-positioning member distal surface.

In a third aspect of the present disclosure, a delivery apparatus to place a prosthesis within a receiving structure may be provided. The delivery apparatus includes an elongated support member comprising a support member distal end. The delivery apparatus further includes a stop cap coupled to the support member distal end, the stop cap comprising a stop cap top opening and including a stop cap transverse dimension that is larger than an inner diameter of a receiving lumen defined by the receiving structure. The delivery apparatus further includes an elongated prosthesis-positioning member including a prosthesis-positioning member distal surface. The delivery apparatus further includes a sheath comprising a sheath lumen, the sheath lumen receiving the prosthesis-positioning member so that the sheath translates longitudinally relative to the prosthesis-positioning member. The delivery apparatus further has a loaded configuration in which the prosthesis is received in the sheath lumen with a proximal end of the prosthesis abutting the prosthesis-positioning member distal surface. The stop cap partially surrounds a portion of the sheath such that a top surface of the sheath is exposed through the stop cap top opening.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 2 is an exploded view of a delivery apparatus;

FIG. 3 is a perspective view of the delivery apparatus of FIG. 2 when assembled;

FIG. 7 is a side view of a connection prosthesis assembly;

FIG. 8 is a longitudinal cross-sectional view of the assembled delivery apparatus of FIG. 3 loaded with the connection prosthesis assembly of FIG. 7;

FIG. 8A is a detail-view of the portion of the loaded delivery apparatus that FIG. 8 indicates is further illustrated in FIG. 8A;

FIG. 9A is a top view of the assembled delivery apparatus of FIG. 3 loaded with the connection prosthesis assembly of FIG. 7;

FIG. 9B is a top view of the assembled delivery apparatus of FIG. 3 loaded with the connection prosthesis assembly of FIG. 7 with the connection prosthesis partially expanded;

FIG. 9C is a top view of the assembled delivery apparatus of FIG. 3 loaded with the connection prosthesis assembly of FIG. 7 with the connection prosthesis fully expanded;

FIG. 9D is a top view of the assembled delivery apparatus of FIG. 3 loaded with the connection prosthesis assembly of FIG. 7 with the connection prosthesis fully deployed;

DETAILED DESCRIPTION OF THE PREFERRED EMBODIMENTS

In the present application, the term "proximal" refers to a direction that is generally upstream to the direction of blood flow during a medical procedure, while the term "distal" refers to a direction that is generally downstream to the direction of blood flow during a medical procedure.

Aspects and embodiments of the present disclosure are configured that provide clinicians with more accurate and more precise medical implant placement, and in doing so, they may provide various benefits. For example, aspects and embodiments of the present disclosure may provide for accurate and precise prosthesis placement by allowing for the surgeon to know the location of a prosthesis relative to a structure into which it is being inserted, despite the unavailability of fluoroscopy or other imaging modalities for visualization of the prosthesis or structure. Aspects and embodiments of the present disclosure may provide for accurate and precise prosthesis placement despite requiring little or no actuation of elements of the device, thus providing a simple user experience. Aspects and embodiments of the present disclosure may provide for accurate and precise prosthesis placement using a delivery apparatus that can flex during placement in order to track through a main body prosthesis or the patient's body to the delivery location. Aspects and embodiments of the present disclosure may provide for accurate and precise prosthesis placement using a delivery apparatus that can flex during placement without buckling. Aspects and embodiments of the present disclosure may provide for accurate and precise prosthesis placement using a delivery apparatus that can easily track through a main body prosthesis without interference of the inside of the main body prosthesis. Those of skill in the art, having the benefit of the present disclosure, may recognize that aspects and embodiments of the present disclosure solve additional problems, provide additional benefits, and may, within the scope of the present disclosure, be practiced in additional technological environments, including during the placement of a variety of medical implants other than prostheses, and during the placement of medical implants using procedures other than a frozen elephant trunk technique.

Figure 1A:
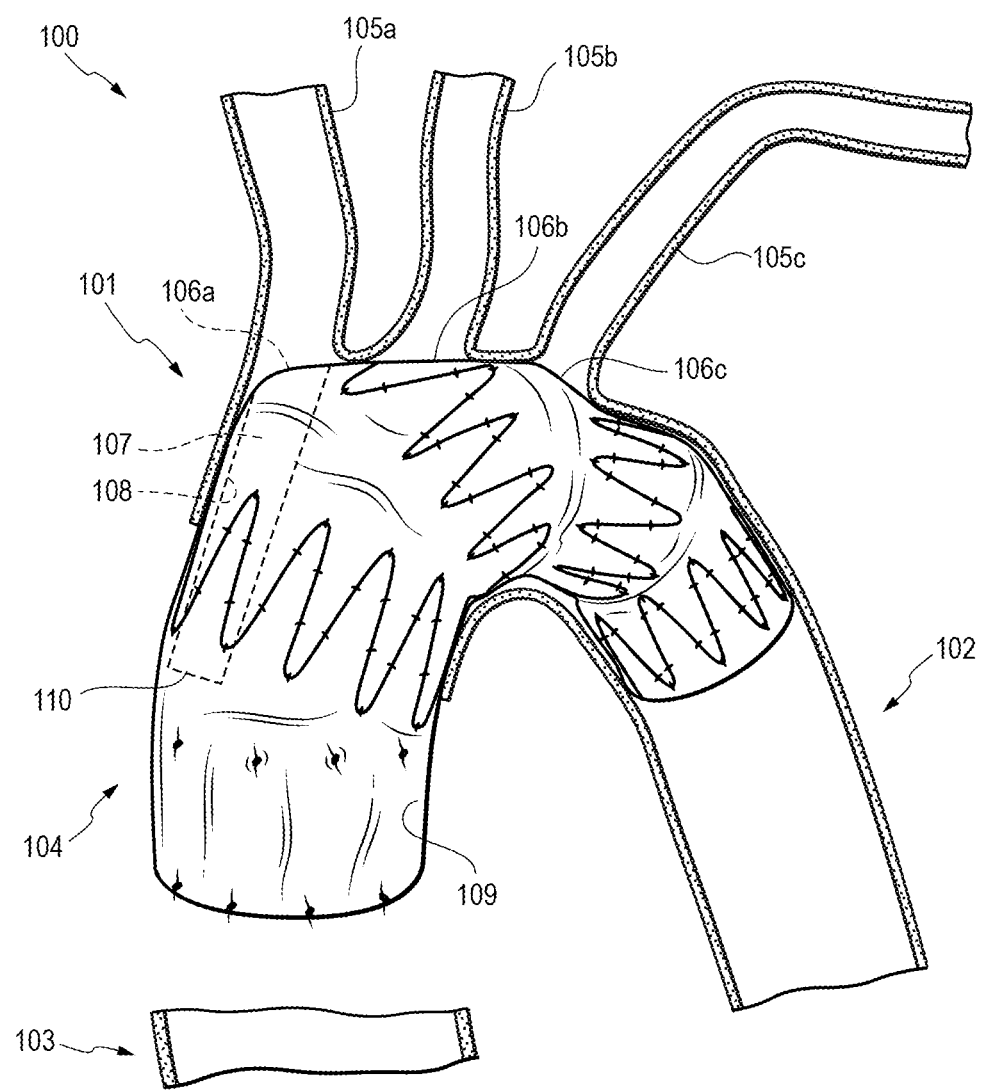
FIG. 1A is a partial sectional view of a partially completed frozen elephant trunk procedure.

An exemplary environment 100 in which a frozen elephant trunk technique has been partially performed is described with reference to FIGS. 1A and 1B. A frozen elephant trunk technique may generally involve: (a) dividing the ascending aorta from the aortic arch 101, the descending aorta 102, and the aortic root 103; (b) placing a first portion of a main body prosthesis 104 within the internal lumen of the descending aorta 102 such that a second portion of the main body prosthesis 104 extends toward the aortic root 103; (c) connecting an end of the first portion of the main body prosthesis 104 to the descending aorta 102; (d) connecting the main body prosthesis 104 to one or more vessels (e.g., brachiocephalic artery 105a, left common carotid artery 105b, and left subclavian artery 105c) that are attached to the roof of the aortic arch 101; and (e) connecting an end of the second portion of the main body prosthesis 104 to the aortic root 103. In FIG. 1A, steps (a)-(c) have been performed.

In the frozen elephant trunk technique, connections of the main body prosthesis 104 to the descending aorta 102 and aortic root 103 may be achieved through anastomoses, while connections of the main body prosthesis 104 to the vessels 105a, 105b, 105c attached to the roof of the aortic arch 101 may be achieved using connection prostheses. The main body prosthesis 104 may include fenestrations 106a, 106b, 106c in its wall, located between the end of the main body prosthesis 104 that will be connected to the aortic root 103 and the end of the main body prosthesis 104 connected to the descending aorta 102, with each fenestration 106a, 106b, 106c corresponding to a respective one of the vessels 105a, 105b, 105c that are attached to the roof of the aortic arch 101. The main body prosthesis 104 may also include a plurality of internal or external branches to facilitate connection, with each branch being a generally tubular structure connected at and extending from its corresponding fenestration. For example, in FIGS. 1A and 1B, an internal branch 107 extends inward into the main body prosthesis 104 from its corresponding fenestration 106a and comprises a receiving lumen 108. In some main body prostheses, an external branch would extend out of the main body prosthesis from its corresponding fenestration. Branches extending from fenestrations 106b and 106c have been omitted to provide a clearer illustration. A branch, e.g., internal branch 107, may be adapted to receive within its lumen, e.g., receiving lumen 108, an expandable connection prosthesis, such that one end of the connection prosthesis is placed in the branch and an opposite end of the connection prosthesis extends out from the main body prosthesis and is received within the given vessel, e.g., 105a. When the connection prosthesis is properly placed within the branch and the given vessel, the connection prosthesis can be expanded to achieve a desired connection of the main body prosthesis to that vessel.

Properly placing a connection prosthesis within a branch and vessel may include establishing a desired overlap between the connection prosthesis and the branch. For example, for a main body prosthesis that includes internal branches, a desired overlap may be one in which a proximal edge of a connection prosthesis is coincident with a proximal edge of the internal branch into which it is placed. However, it may be difficult for the clinician to align the proximal edge of the connection prosthesis and the proximal edge of the internal branch, because the proximal edge of the internal branch may be surrounded by the primary main body prosthesis and thus not visible to the clinician, and because fluoroscopy may not be available to assist in visualization.

Embodiments of a medical implant delivery apparatus and associated methods are described with reference to FIGS. 2-4, 5A-5C, 6-8, 8A, 9A-9D, and 10A-10E, which illustrate delivery apparatus 200 and associated methods. As illustrated for example in an exploded view in FIG. 2 and a perspective view in FIG. 3, delivery apparatus 200 includes stop mechanism 210, sheath assembly 260, prosthesis-positioning member 270, and handle assembly 280. Delivery apparatus 200 is compatible with connection prosthesis assembly 290, which includes connection prosthesis 291, cannula 292, tip 293, and connection prosthesis proximal edge 294, as illustrated for example in FIGS. 7, 8, 8A, 9A-9D and 10A-10D. As explained in further detail below, aspects of that compatibility may allow a clinician to accurately and precisely place connection prosthesis 291 in receiving lumen 108 of internal branch 107, despite an inability of the clinician to visualize the relative positions of the connection prosthesis 291 and internal branch 107.

Stop mechanism 210, particularly in cooperation with prosthesis-positioning member 270 as discussed further below, may allow a clinician to tactilely determine when connection prosthesis 291 has been sufficiently inserted within receiving lumen 108 of internal branch 107. Stop mechanism 210 includes support member 220, stop cap 230, and spine portion 240. The tactile feedback mentioned above is generated through the force of the clinician contacting internal branch 107 with stop cap 230, as illustrated, for example in FIGS. 10A-10C. Moreover, the design of stop mechanism 210 may also allow the clinician to easily track connection prosthesis 291 through main body prosthesis 104 and into lumen 108 of internal branch 107.

As illustrated for example in FIGS. 2-4, 6, 8, 8A, 9A-9D, and 10A-10D, support member 220 is an elongated structure that extends longitudinally from support member proximal end 221 to support member distal end 222. Stop cap 230 is disposed at support member distal end 222. Stop cap 230 may be affixed to or otherwise coupled to or integral with support member distal end 222. Support member 220 includes a bowed section 223 leading to support member proximal end 221. Support member 220 may be a wire that is sufficiently stiff to support stop cap 230 and sufficiently flexible to track within a curved lumen 109 defined by main body prosthesis 104. Support member 220 is depicted as having a round shape in transverse cross-section. However in some embodiments of stop mechanisms, a support member may be of other shapes in transverse cross-section, including rectangular. Additionally, although FIGS. 2-4, 6, 8, 8A, 9A-9D, and 10A-10D illustrate delivery apparatus 200 as having a single support member 220, in some embodiments a stop mechanism could include a plurality of support members, for example to increase the rigidity of the stop mechanism.

As illustrated for example in FIGS. 4 and 10A-10D, stop cap 230 includes at least one transverse dimension that is larger than the inner diameter of receiving lumen 108, thereby preventing stop cap 230 from entering receiving lumen 108. A transverse dimension is one that extends transversely to a longitudinal axis of delivery apparatus 200. For example, stop cap width 231 is a transverse dimension because it extends perpendicularly to a longitudinal axis of delivery apparatus 200. Additionally, stop cap width 231 is larger than the inner diameter of receiving lumen 108. In some embodiments, additional or alternative transverse dimensions, e.g., stop cap height 232, etc., may be larger than the inner diameter of receiving lumen 108.

Stop cap 230 extends longitudinally from stop cap distal surface 233 to stop cap proximal surface 234. In some embodiments, at least one stop cap transverse dimension that is larger than the inner diameter of receiving lumen 108 is longitudinally disposed at the stop cap distal surface 233. For example, stop cap width 231 and/or stop cap height 232 may be longitudinally disposed at the stop cap distal surface 233. This adapts stop cap distal surface 233 for abutting a proximal edge 110 of inner branch 107 when stop cap distal surface 233 is tracked towards it. That interaction prevents stop cap 230 from entering the receiving lumen 108 and also generates a contact force between stop cap 230 and inner branch 107 that alerts the clinician to the relative locations of inner branch 107 and stop mechanism 210.

Figure 4:
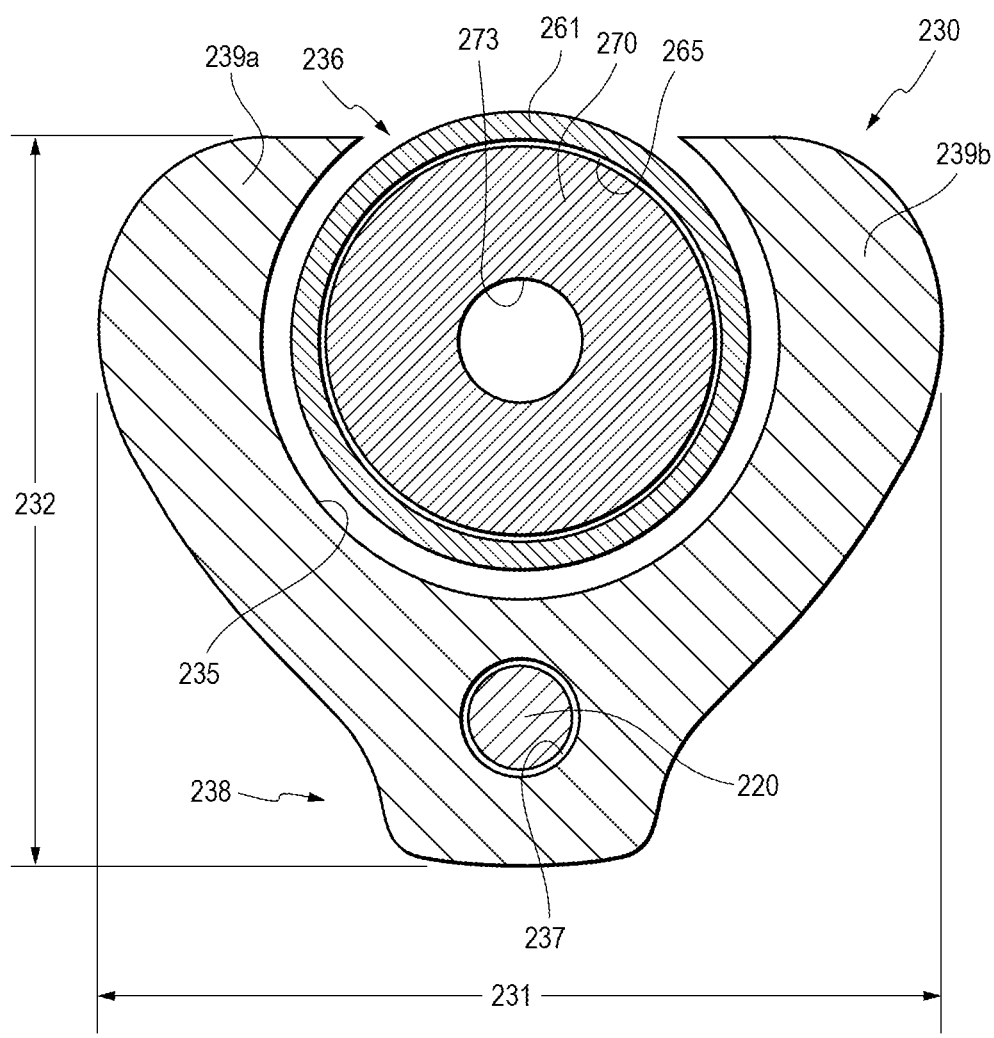
FIG. 4 is a transverse cross-sectional view through the assembled delivery apparatus of FIG. 3 at the stop cap.

Stop cap 230 includes a variety of additional aspects that may produce clinical benefits. Stop cap 230 comprises a stop cap aperture 235 extending longitudinally from stop cap distal surface 233 to stop cap proximal surface 234. Stop cap 230 also comprises a stop cap top opening 236 that connects with stop cap aperture 235. Stop cap 230 is illustrated in FIGS. 2-4, and 10A as having a generally heart-shaped circumference when viewed along a longitudinal axis of delivery apparatus 200. For example, as best illustrated in FIG. 4, stop cap 230 includes stop cap bottom portion 238 and a pair of stop cap arms 239a, 239b. Stop cap arms 239a, 239b curve outward from stop cap bottom portion 238 and extend upward from stop cap bottom portion 238, tapering to stop cap top opening 236. The inner surface of stop cap bottom portion 238 and the inner surfaces of stop cap arms 239a, 239b help to define the stop cap aperture 235.

Figure 5A:
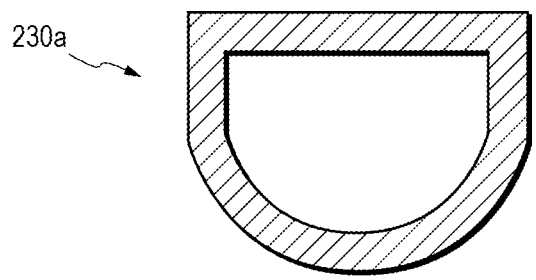
FIG. 5A is a transverse cross-sectional view through a D-shaped stop cap.
Figure 5B:
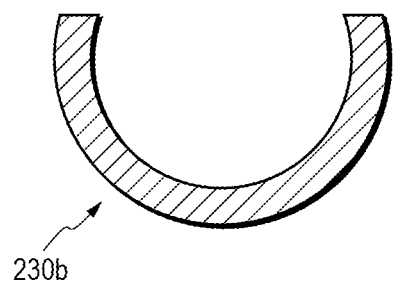
FIG. 5B is a transverse cross-sectional view through a C-shaped stop cap.
Figure 5C:
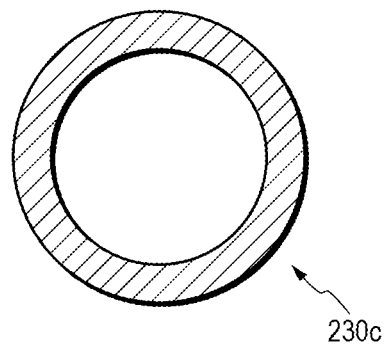
FIG. 5C is a transverse cross-sectional view through a ring-shaped stop cap.

In some embodiments, a stop cap may be formed to have a circumference of another shape when viewed along a longitudinal axis of delivery apparatus 200. Those other shapes may include, for example: D-shaped, e.g., as illustrated in FIG. 5A in stop cap 230a; C-shaped, e.g., as illustrated in FIG. 5B in stop cap 230b; or ring-shaped e.g., as illustrated in FIG. 5C in stop cap 230c. Notably, stop caps which, when viewed along a longitudinal axis of delivery apparatus 200, have a shape in which the height of a first portion of the stop cap extending above a longitudinal axis of the sheath when the sheath is received in the stop cap is less than the height of a second portion of the stop cap extending below the longitudinal axis of the sheath when the sheath is received in the stop cap (for example: generally heart-shaped as in stop cap 230; D-shaped as in stop cap 230a; or C-shaped as in stop cap 230b) may allow for better tracking of the stop mechanism within main body prosthesis 104, as further explained below with reference to FIGS. 10A-10D.

Figure 6:
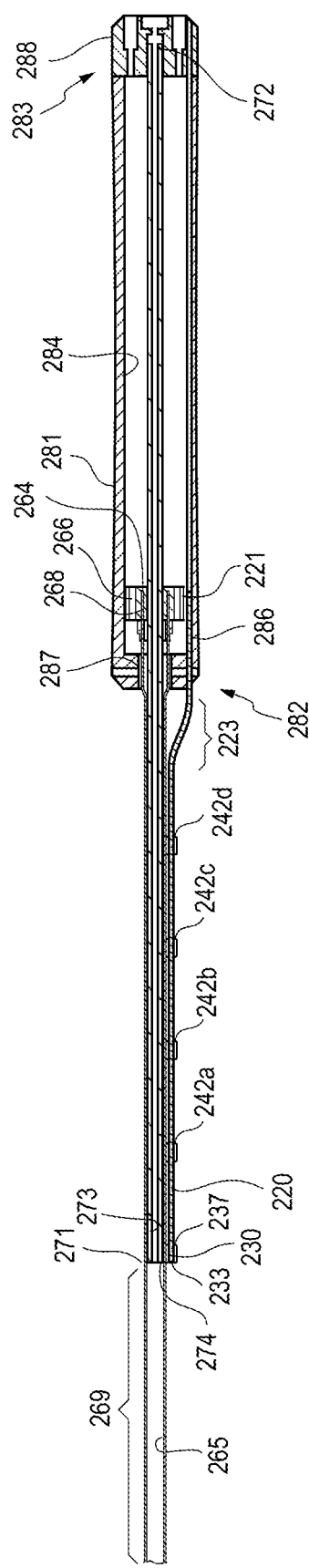
FIG. 6 is a longitudinal cross-sectional view through the assembled delivery apparatus of FIG. 3.

Stop cap 230 also comprises a stop cap lumen 237 extending distally from stop cap proximal surface 234 and into stop cap 230, for example as illustrated in FIGS. 6, 8, and 8A. Stop cap lumen 237 is configured to receive support member distal end 222. In some embodiments, support member distal end 222 may be affixed within stop cap lumen 237. In other embodiments, a stop cap may be coupled to a support member distal end in alternative manners.

As noted above, spine portion 240 is another component of stop mechanism 210. Spine portion 240 is configured to reinforce support member 220 against buckling when stop cap 230 is pressed longitudinally against an object, for example the proximal edge 110 of inner branch 107, for example as illustrated in FIGS. 10A-10D. FIGS. 2, 3, 6, 8, 8A, 9A-9D, and 10B-10D depict spine portion 240 as including a plurality of spine members 241a, 241b, 241c, 241d affixed or otherwise coupled to support member 220 between stop cap 230 and support member proximal end 221. Each of the plurality of spine members 241a, 241b, 241c, 241d is depicted as being identical in shape and size to stop cap 230, with the exception being that while stop cap lumen 237 is depicted as extending longitudinally only partially through stop cap 230, each of the plurality of spine members 241a, 241b, 241c, 241d includes a respective spine member lumen 242a, 242b, 242c, 242d that extends longitudinally through the entire respective spine member. Support member 220 then passes through each of spine member lumens 242a, 242b, 242c, 242d and may be affixed within them. Additionally, each of the plurality of spine members 241a, 241b, 241c, 241d is longitudinally spaced apart from each other spine member of the plurality of spine members 241a, 241b, 241c, 241d, and from stop cap 230. The spacing of the plurality of spine members 241a, 241b, 241c, 241d is configured to provide the reinforcement of support member 220 against buckling that is discussed above, while still allowing for sufficient flexibility for stop mechanism 210 to track within the curved lumen 109 defined by main body prosthesis 104, for example as illustrated in FIGS. 10A-10D.

Although spine portion 240 as illustrated in FIGS. 2, 3, 6, 8, 9A-9D, and 10B-10D provides a desirable combination of buckling protection and flexibility for tracking, other embodiments of a spine portion may be suitable. For example, embodiments of a spine portion may include any appropriate number of spine members, including a single spine member. In some embodiments, a spine portion may include spacing of spine members that is different from the spacing in spine portion 240. In some embodiments, the one or more spine members of a spine portion may have shapes and/or sizes that differ from the shape and size of stop cap 230. For example, the one or more members of a spine portion may have shapes and/or sizes identical to stop cap 230a, stop cap 230b, or stop cap 230c. In some embodiments, spine members of a spine portion may have shapes and/or sizes that differ from the shapes and/or sizes of the other spine members of that spine portion. Furthermore, in some stop mechanism embodiments, a spine portion may be omitted entirely. For example, in some embodiments the stop mechanism may include only a stop cap attached to the distal end of one or more support members.

Sheath assembly 260 is generally adapted to hold connection prosthesis 291 in a reduced state and guide it into receiving lumen 108 of internal branch 107, for example as illustrated in FIGS. 9A-9D and 10A-10D. Sheath assembly 260 also cooperates with prosthesis-positioning member 270 and handle assembly 280 to deploy connection prosthesis 291 when it has been properly placed. Sheath assembly 260 includes sheath 261 and sheath retraction structure 262, for example as illustrated in FIG. 2.

Sheath 261 is a generally tubular elongated structure extending from sheath distal end 263 to sheath proximal end 264 and comprising sheath lumen 265. Sheath lumen 265 may be adapted to receive and retain expandable connection prosthesis 291 in a reduced configuration, while still allowing sheath 261 to longitudinally translate relative to connection prosthesis 291 for deployment. Sheath 261 may be made of a clear material. FIGS. 3, 4, 6, 8, 8A, and 9A-9C depict sheath 261 as being adapted to be received within stop cap aperture 235 and the corresponding spine member apertures of spine members 241a, 241b, 241c, 241d, such that sheath 261 can also longitudinally translate relative to stop mechanism 210.

Sheath retraction structure 262 is affixed at or otherwise coupled to sheath proximal end 264 and includes a sheath retraction body 266 and sheath retraction protrusions 267a, 267b that extend transversely outward from sheath retraction body 266, illustrated for example in FIG. 2. Sheath retraction body 266 comprises a sheath body lumen 268 passing longitudinally therethrough.

Prosthesis-positioning member 270 is illustrated in FIGS. 2-4, 6, 8, and 8A, and generally serves to maintain a desired relative position between connection prosthesis 291 and stop cap 230, so that when the clinician feels the tactile feedback of stop cap 230 contacting internal branch 107, the clinician can be confident that the connection prosthesis is properly inserted within receiving lumen 108. Prosthesis-positioning member 270 is a generally tubular elongated structure extending from prosthesis-positioning member distal end 271 to prosthesis-positioning member proximal end 272 and comprising prosthesis-positioning member lumen 273. Prosthesis-positioning member 270 includes a distally facing distal surface 274 at prosthesis-positioning member distal end 271. Prosthesis-positioning member lumen 273 may be adapted to receive a cannula 292 of connection prosthesis assembly 290. Prosthesis-positioning member 270 is adapted to be received within both sheath lumen 265 and sheath body lumen 268 such that sheath assembly 260 can longitudinally translate relative to prosthesis-positioning member 270.

Handle assembly 280 is illustrated in FIGS. 2, 3, 6, 8, and 9A-9D, and generally acts to support previously discussed components of delivery apparatus 200 and cooperates with sheath assembly 260 and prosthesis-positioning member 270 to effect deployment of connection prosthesis 291. Handle assembly 280 includes a handle housing 281 extending longitudinally from handle distal end 282 to handle proximal end 283 and comprising a handle lumen 284. Handle lumen 284 is adapted to receive sheath retraction body 266 so that sheath retraction structure 262 can longitudinally translate within handle assembly 280 and along prosthesis-positioning member 270. Handle housing 281 further comprises a pair of longitudinally extending guidance channels 285a, 285b adapted to respectively receive sheath retraction protrusions 267a, 267b such that sheath retraction protrusions 267a, 267b can longitudinally translate therein. Sheath retraction protrusions 267a, 267b extend transversely out of handle housing 281 through guidance channels 285a, 285b so the clinician can manipulate one or both of them to retract sheath retraction structure 262 and deploy connection prosthesis 291.

Handle housing 281 also comprises a support member coupling lumen 286 extending proximally into handle housing 281 from handle distal end 282. Support member coupling lumen 286 is adapted to receive support member proximal end 221. Support member proximal end 221 may be affixed within or otherwise coupled to support member coupling lumen 286. Handle housing 281 further comprises a sheath coupling lumen 287 adapted to allow sheath 261 to longitudinally translate relative thereto, such that upon assembly, sheath 261 passes through, and can longitudinally translate relative to, stop cap aperture 235 and the corresponding spine member apertures of spine members 241a, 241b, 241c, 241d. Handle assembly 280 further includes an end cap 288 that can be secured to handle housing 281 to close handle assembly 280 after sheath 261 and sheath retraction structure 262 have been inserted in handle housing 281 and prosthesis-positioning member 270 has been inserted in sheath assembly 260 as shown in FIGS. 2 and 3.

Once delivery apparatus 200 has been assembled in accordance with the above description and for example as depicted in FIGS. 3 and 6, prosthesis-positioning member 270 extends within sheath 261 and along support member 220 such that distal surface 274 of prosthesis-positioning member 270 is disposed at a position longitudinally coincident with stop cap distal surface 233. For the purposes of the present disclosure, two points, surfaces, structures, etc., may be considered to be longitudinally coincident with each other if the longitudinal offset between them is within a range of tolerance of being precisely longitudinally coincident, where the range of tolerance is less than or equal to 2 millimeters. An acceptable range of tolerance may be less than 2 millimeters depending upon the given clinical application's allowable longitudinal offset between the proximal edge of the placed prosthesis and the proximal edge of the receiving structure. Accordingly, this disclosure includes embodiments in which distal surface 274 of prosthesis-positioning member 270 is precisely longitudinally coincident with (i.e., has no longitudinal offset from) stop cap distal surface 233.

Sheath 261 is arranged such that sheath distal end 263 is disposed at a position longitudinally distal to stop cap distal surface 233. A portion 269 of sheath lumen 265 distal to stop cap distal surface 233 is not filled by prosthesis-positioning member 270, allowing portion 269 to receive connection prosthesis 291 such that connection prosthesis proximal edge 294 abuts distal surface 274, as depicted for example in FIGS. 8, 8A, 9A, and 10B. For the purposes of the present disclosure, a connection prosthesis proximal edge and a distal surface of a prosthesis positioning member may be considered to be abutting each other if the longitudinal offset between them is within a range of tolerance of being in contact with each other, where the range of tolerance is less than or equal to 2 millimeters. An acceptable range of tolerance may be less than 2 millimeters depending upon the given clinical application's allowable longitudinal offset between the proximal edge of the placed prosthesis and the proximal edge of the receiving structure. Accordingly, this disclosure includes embodiments in which connection prosthesis proximal edge 294 contacts distal surface 274.

In this loaded configuration, i.e., loaded delivery apparatus 300, cannula 292 may also be extending proximally through prosthesis-positioning member lumen 273, and tip 293 may be positioned distal to sheath distal end 263. With delivery apparatus 200 in the loaded configuration, i.e., loaded delivery apparatus 300, shown in FIGS. 8, 8A, 9A, and 10B, a clinician may use delivery apparatus 200 to accurately and precisely place connection prosthesis 291 in receiving lumen 108 of internal branch 107.

Although exemplary delivery apparatus 200 has generally been described in the present disclosure in the context of clinical applications for which it may be desirable to minimize the longitudinal offset between the proximal edge of the placed prosthesis and the proximal edge of the receiving structure, the present disclosure includes embodiments adapted to use in clinical applications in which a specific longitudinal offset between the proximal edge of the placed prosthesis and the proximal edge of the receiving structure may be desired. Given the benefit of the present disclosure, those skilled in the art may recognize how a delivery apparatus similar to delivery apparatus 200 could be produced to provide the desired specific longitudinal offset between the proximal edge of the placed prosthesis and the proximal edge of the receiving structure, e.g., by changing the longitudinal position of the distal surface of the prosthesis-positioning member relative to the stop cap distal surface. For example, in an exemplary clinical application in which it is desired for the proximal edge of the placed prosthesis to be positioned 5 millimeters distal to the proximal edge of the receiving structure, a prosthesis-positioning member that is 5 millimeters longer than prosthesis-positioning member 270 could be used so that its distal surface is 5 millimeters distal to the stop cap distal surface.

Figure 1B:
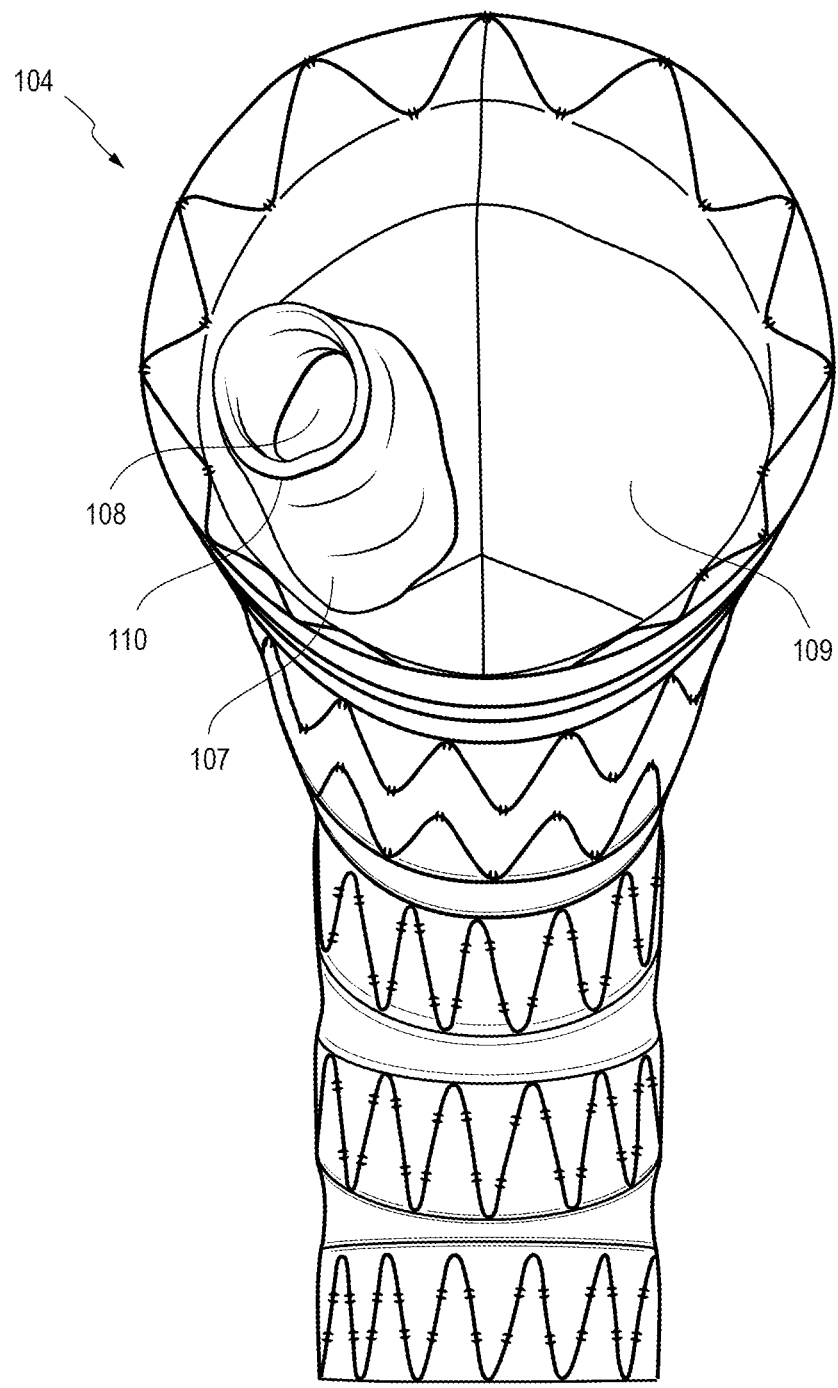
FIG. 1B is a perspective view of a main body prosthesis with an internal branch as also shown in FIG. 1A.
Figure 10A:
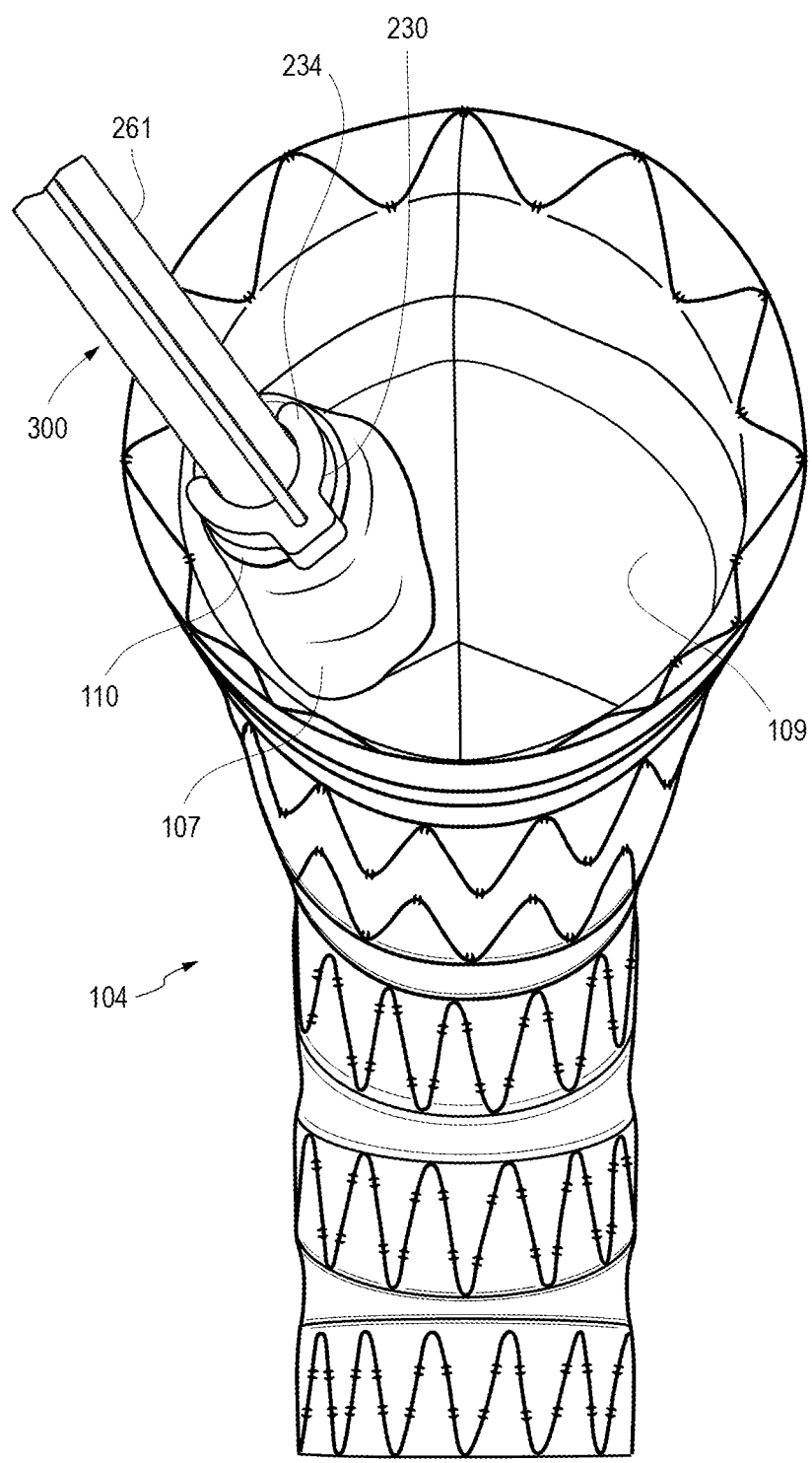
FIG. 10A is a perspective view of a partially completed frozen elephant trunk procedure illustrating a delivery apparatus being received in an internal branch with the delivery apparatus being in an inserted configuration.
Figure 10B:
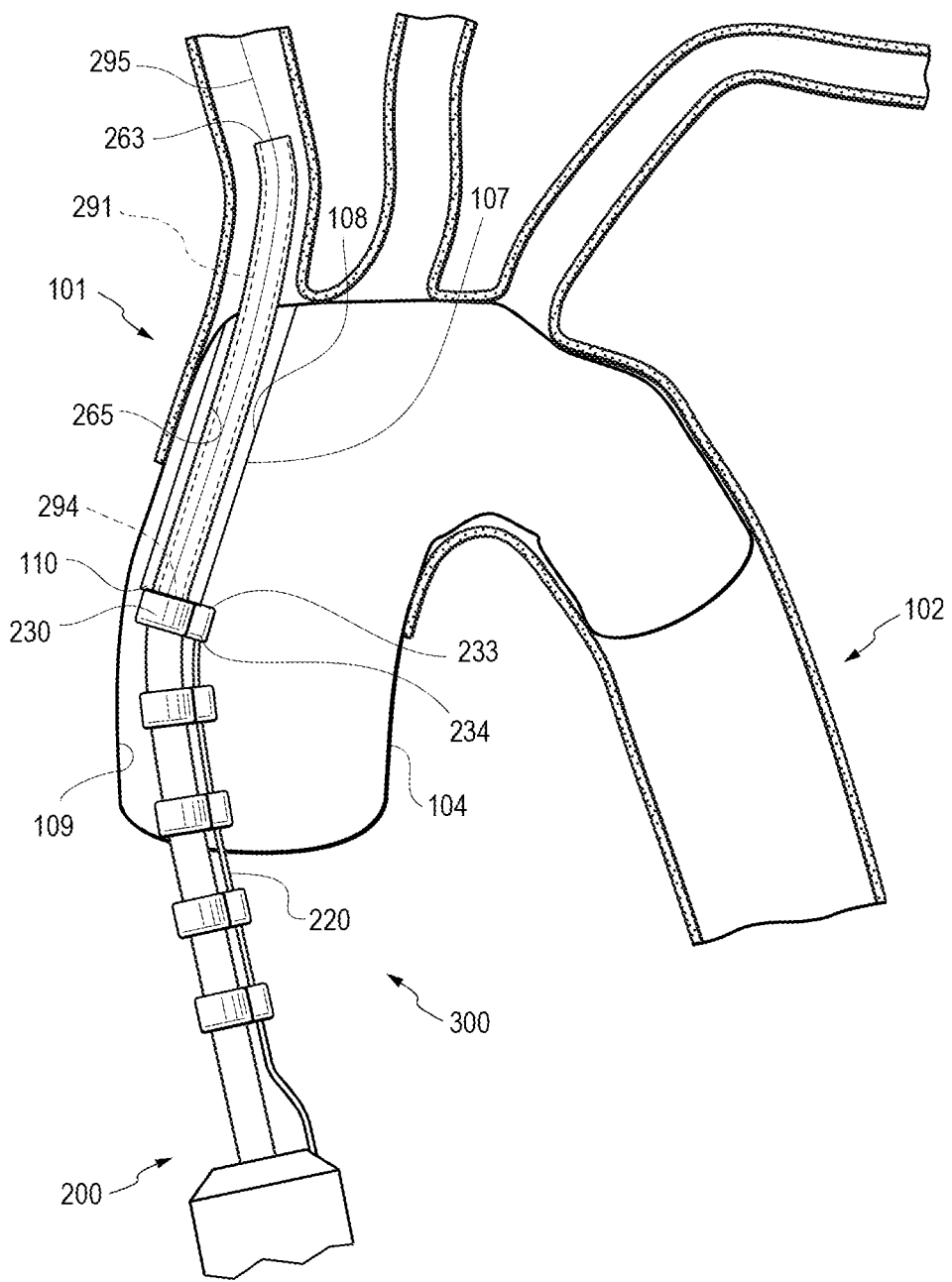
FIG. 10B is a partial cross-sectional view of the partially completed frozen elephant trunk procedure of FIG. 10A with the delivery apparatus being in the inserted configuration.

FIGS. 10A-10E depict an environment similar to the exemplary environment 100 of FIGS. 1A and 1B, but add a cross-sectional view through main body prosthesis 104 and show delivery apparatus 200 in various states during an exemplary frozen elephant trunk procedure. In FIGS. 9A and 10B, delivery apparatus 200 is loaded with connection prosthesis 291 (omitting cannula 292 and tip 293 in FIG. 10B for clarity), resulting in loaded delivery apparatus 300. Sheath distal end 263 tracks along preloaded guidewire 295 into curved lumen 109 of main body prosthesis 104 and then into receiving lumen 108 of internal branch 107, until stop cap distal surface 233 has contacted proximal edge 110 of inner branch 107, placing delivery apparatus 200 in an inserted configuration, examples of which are illustrated in FIGS. 10A and 10B. At least one transverse dimension (e.g., stop cap height 232) is larger than the inner diameter of receiving lumen 108, so stop mechanism 210 stops moving. Spine portion 240 may flex but does not buckle when the clinician applies force to stop cap 230, so the clinician reaches the inner branch 107 while also receiving meaningful tactile feedback. Moreover, because connection prosthesis proximal end 294 is longitudinally coincident with stop cap distal surface 233, which is itself abutting proximal edge 110 of inner branch 107, the clinician can be confident that connection prosthesis proximal end 294 is also longitudinally coincident with proximal edge 110 of inner branch 107, even without being able to see the connection prosthesis 291 or inner branch 107.

The configurations in FIGS. 10A-10D also illustrate why stop caps that have shapes in which, when viewed along a longitudinal axis of delivery apparatus 200, the height of a first portion of the stop cap extending above a longitudinal axis of the sheath when the sheath is received in the stop cap is less than the height of a second portion of the stop cap extending below the longitudinal axis of the sheath when the sheath is received in the stop cap (for example: generally heart-shaped as in stop cap 230; D-shaped as in stop cap 230a; or C-shaped as in stop cap 230b) may allow for better tracking of a stop mechanism within main body prosthesis 104 than stop mechanisms whose caps lack that feature. For example, as depicted in FIGS. 10A-10D, inner branch 107 is located closely to a wall of curved lumen 109, and if stop cap 230 did not have a shape in which the height of a first portion of the stop cap extending above a longitudinal axis of the sheath when the sheath is received in the stop cap is less than the height of a second portion of the stop cap extending below the longitudinal axis of the sheath when the sheath is received in the stop cap, the top of stop cap 230 would be more likely to catch on the wall of curved lumen 109. However, given the shape of stop cap 230, delivery apparatus 200 can be rotated such that stop cap top opening 236 is facing the wall of curved lumen 109 and more clearance is available. This can help prevent stop cap 230 from catching on the wall of curved lumen 109.

Figure 10C:
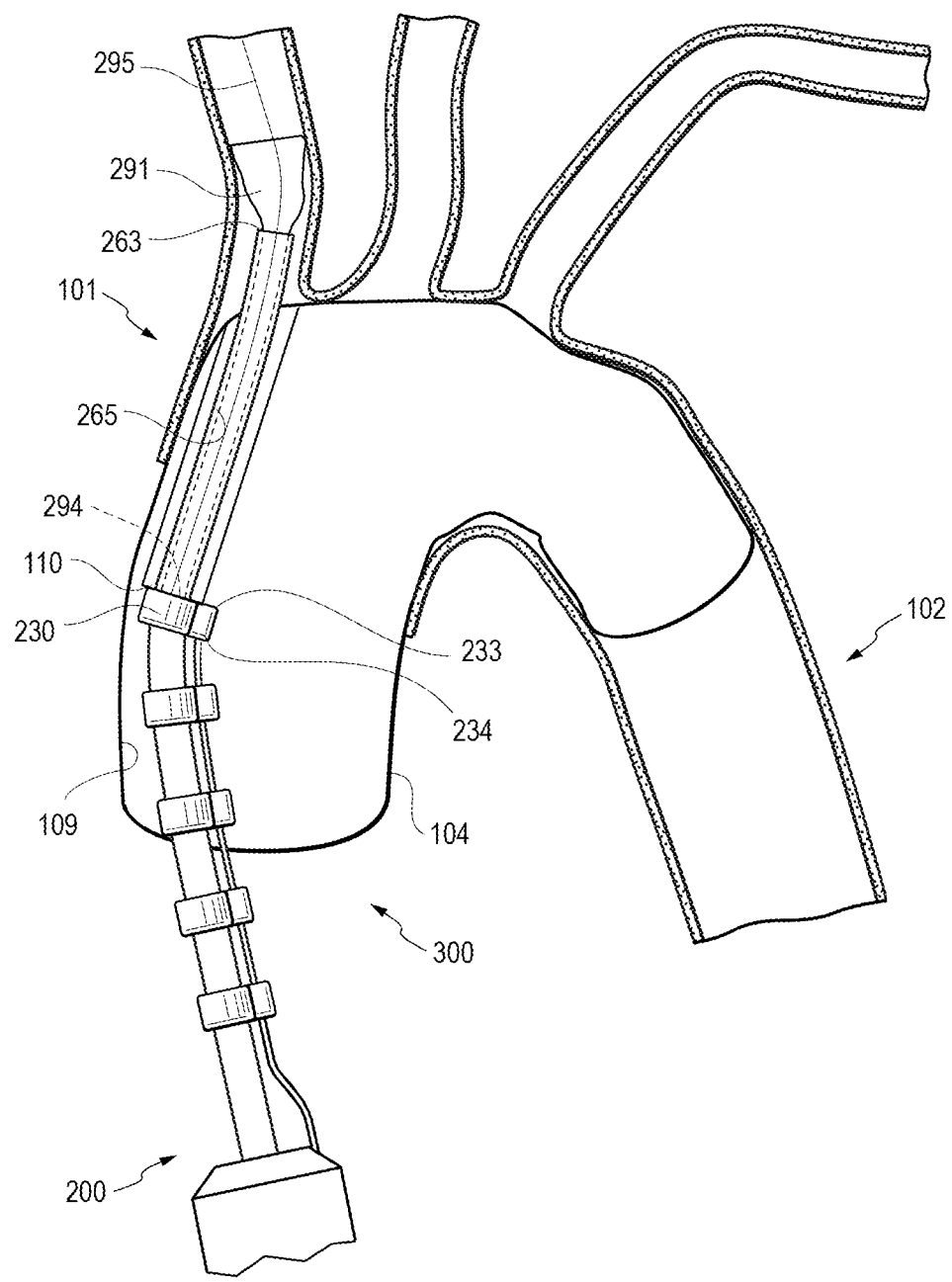
FIG. 10C is a partial cross-sectional view of the partially completed frozen elephant trunk procedure of FIG. 10A with the connection prosthesis partially expanded.

In FIGS. 9B and 10C, the clinician begins to deploy connection prosthesis 291, by retracting sheath 261 relative to prosthesis-positioning member 270 using sheath retraction structure 262, e.g., by pulling back on one or more of sheath retraction protrusions 267a, 267b. Connection prosthesis 291 is thus exposed and begins to expand within brachiocephalic artery 105a. Stop cap 233 continues to abut proximal edge 110 of inner branch 107, which helps to maintain the desired alignment of connection prosthesis proximal end 294 and proximal edge 110 of inner branch 107.

Figure 10D:
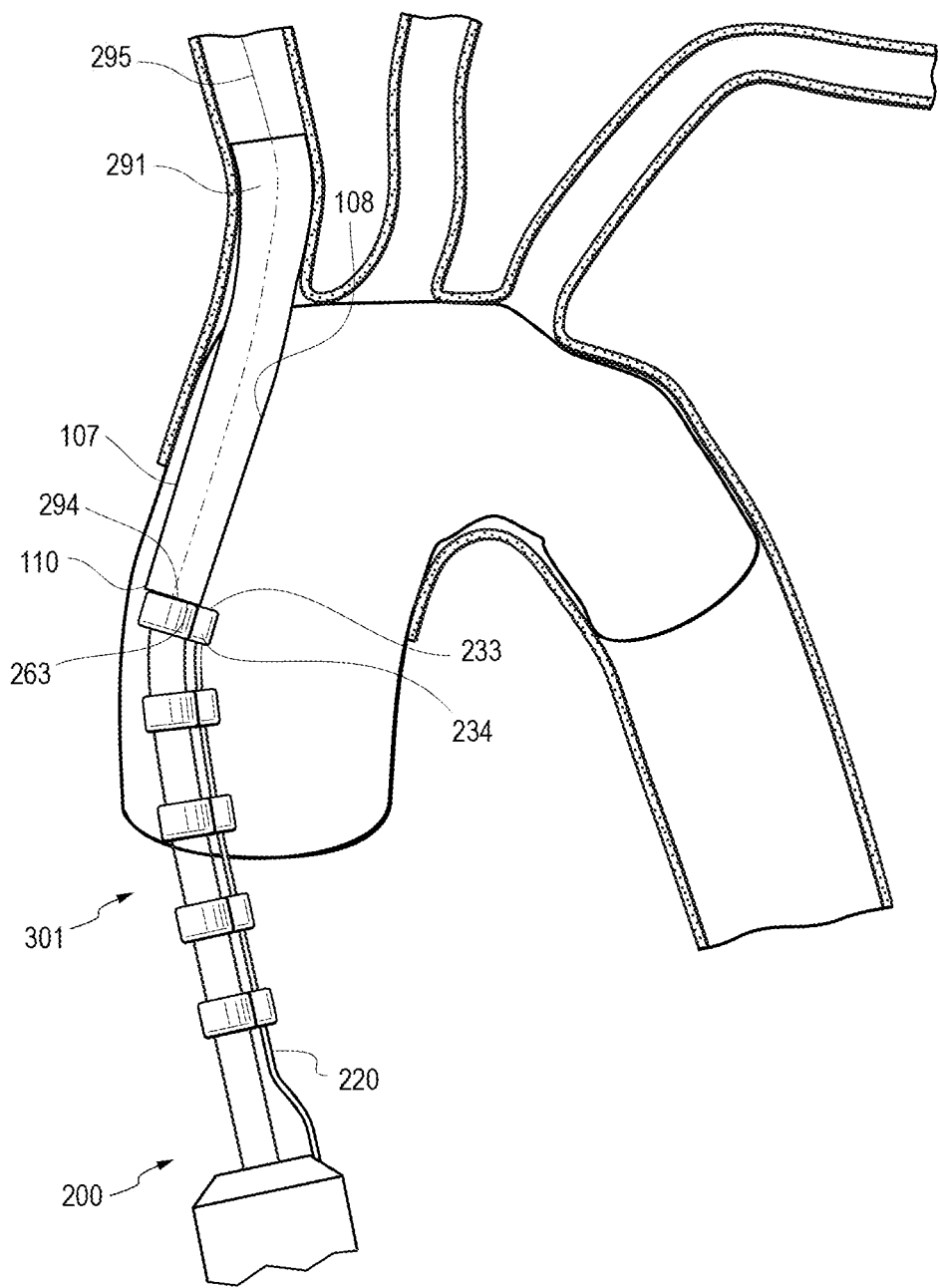
FIG. 10D is a partial cross-sectional view of the partially completed frozen elephant trunk procedure of FIG. 10A with the connection prosthesis fully expanded.
Figure 10E:
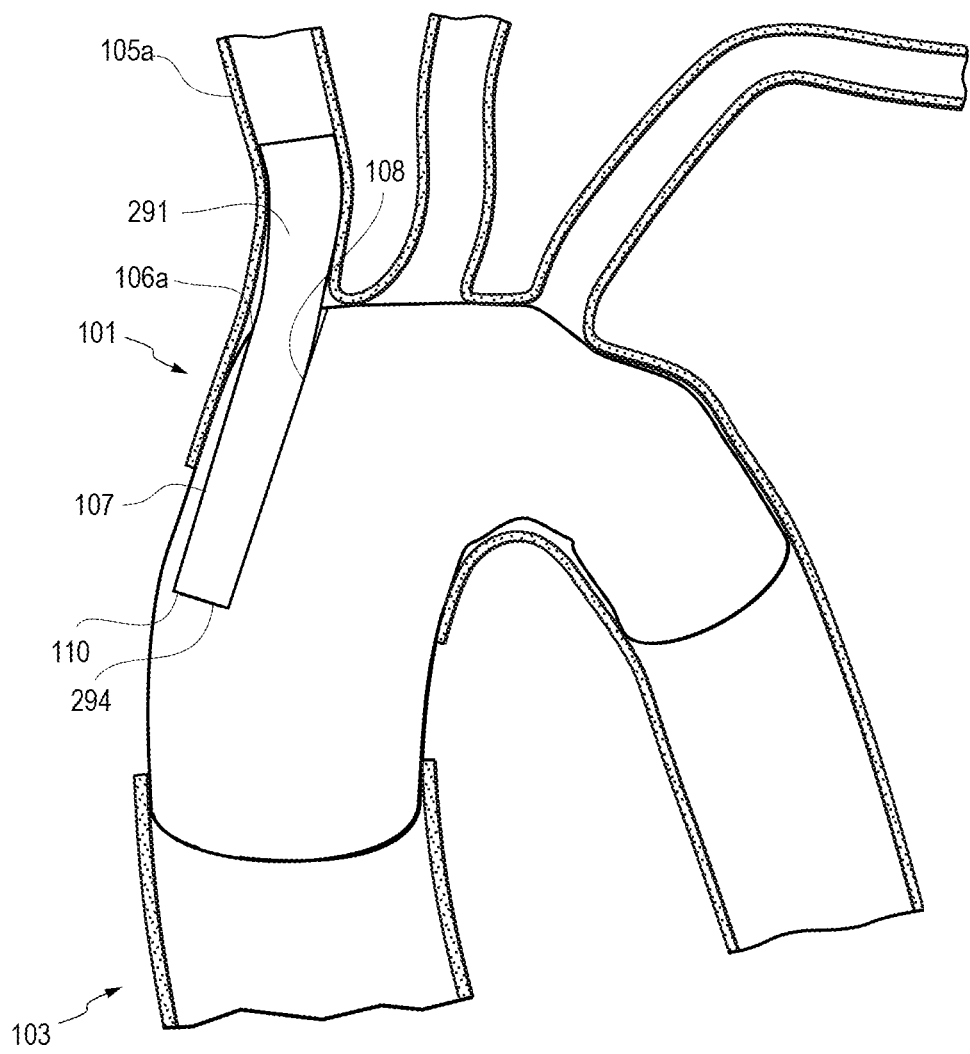
FIG. 10E is a partial cross-sectional view of the partially completed frozen elephant trunk procedure of FIG. 10A with the connection prosthesis fully deployed and the delivery apparatus removed.

In FIGS. 9C and 10D, sheath 261 completely retracts, allowing connection prosthesis 291 to fully expand within brachiocephalic artery 105a and within receiving lumen 108 of inner branch 107. Connection prosthesis proximal end 294 continues to be longitudinally coincident with proximal edge 110 of inner branch 107, resulting in a desired overlap of connection prosthesis 291 with brachiocephalic artery 105a and inner branch 107, and thus a strong and well-sealed connection between main body prosthesis 104 and brachiocephalic artery 105a.

In some embodiments, similar steps would then be performed to connect left common carotid artery 105b and left subclavian artery 105c with their corresponding branches (not shown). Then, in FIG. 10E, delivery apparatus 200 is withdrawn from main body prosthesis 104, and aortic root 103 is connected to main body prosthesis 104.

Although specific examples in the instant disclosure have generally focused on an open cardiothoracic surgical procedure, i.e., a frozen elephant trunk procedure, those of skill in the art may recognize that aspects of the instant disclosure may be applicable to placing connection prostheses during endovascular procedures. Additionally, those skilled in the art may recognize that aspects of the instant disclosure may be applicable to placing types of prostheses other than connection prostheses, and to placing other types of medical implants.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:
1. A system to place a prosthesis within a receiving structure, the system comprising:
the receiving structure having a receiving lumen, the receiving lumen having proximal and distal ends, and including a length of a substantially uniform inner diameter extending at least partly between the proximal and distal ends of the receiving lumen, wherein the receiving structure is an internal branch disposed within a main body prosthesis;
an elongated support member comprising a support member distal end;
a stop cap disposed at the support member distal end, the stop cap comprising a stop cap transverse dimension that is larger than an inner diameter of the receiving lumen of the receiving structure;
an elongated prosthesis-positioning member comprising a prosthesis-positioning member distal surface and extending along the support member and the stop cap so that a distal surface of the prosthesis-positioning member is configured to be selectively disposed either at a position longitudinally coincident with a portion of the stop cap or at a preselected distance distal to a distal end of the stop cap; and
a sheath comprising a sheath lumen, the sheath lumen receiving the prosthesis-positioning member so that the sheath translates longitudinally relative to the prosthesis-positioning member,
wherein the system has a loaded configuration in which the prosthesis is received in the sheath lumen with a proximal end of the prosthesis abutting the prosthesis-positioning member distal surface,
wherein the system is adapted to be operated in a first configuration such that the proximal end of the prosthesis is deployed substantially coincident with the proximal end of the receiving lumen when the distal surface of the prosthesis-positioning member is disposed at the position longitudinally coincident with the distal end of the stop cap, and
wherein the system further is adapted to be operated in a second configuration such that the proximal end of the prosthesis is deployed a predetermined distance distally beyond the proximal end of the receiving lumen, along the length between the proximal and distal ends of the receiving lumen, when the distal surface of the prosthesis-positioning member is disposed a corresponding length beyond the distal end of the stop cap.

2. The system of claim 1, wherein:
the stop cap further comprises a stop cap distal surface;
the stop cap transverse dimension is disposed at the stop cap distal surface; and
the system has an inserted configuration in which:
the stop cap distal surface abuts an edge of the receiving structure surrounding the receiving lumen,
a portion of the sheath enters the receiving lumen, and
the stop cap is prevented from entering the receiving lumen.

3. The system of claim 1, wherein:
the stop cap further comprises a stop cap distal surface; and
the prosthesis-positioning member distal surface is disposed at a position longitudinally coincident with the stop cap distal surface.

4. The system of claim 1, wherein the stop cap further comprises a stop cap distal surface and a stop cap proximal surface, and comprises a stop cap aperture extending longitudinally from the stop cap distal surface to the stop cap proximal surface.

5. The system of claim 4, wherein the sheath and prosthesis-positioning member extend longitudinally within the stop cap aperture.

6. The system of claim 1, wherein the prosthesis is a connection prosthesis.

7. The system of claim 1, wherein the stop cap is affixed at the support member distal end.

8. The system of claim 1, wherein proximal retraction of the sheath relative to the prosthesis and the prosthesis-positioning member deploys the prosthesis when the system is in the loaded configuration.

9. The system of claim 1, further comprising a sheath retraction structure and a handle, wherein:
- the handle comprises a handle housing including a handle lumen and a longitudinally extending guidance channel;
- the sheath retraction structure is coupled to the sheath proximal end and comprises:
  - a sheath retraction body received within the handle lumen; and
  - a sheath retraction protrusion received within the guidance channel; and
- when the prosthesis is received in the sheath lumen, proximal retraction of the sheath retraction structure relative to the handle causes the sheath to retract in a proximal direction relative to the prosthesis and the prosthesis-positioning member to deploy the prosthesis.

10. The system of claim 9, wherein:
the prosthesis-positioning member extends into the handle lumen; and
the sheath retraction structure comprises a sheath retraction structure lumen that receives the prosthesis-positioning member so that the sheath retraction structure retracts in a proximal direction along the prosthesis-positioning member.

* * * * *